United States Patent
Sweat et al.

(10) Patent No.: US 10,166,322 B2
(45) Date of Patent: Jan. 1, 2019

(54) GAIN IN SEPARATION PROCESSES WITH CONTROL LOOP

(71) Applicant: Terumo BCT, Inc., Lakewood, CO (US)

(72) Inventors: William Sweat, Lakewood, CO (US); Christopher Corey Howells, Lakewood, CO (US)

(73) Assignee: Terumo BCT, Inc., Lakewood, CO (US)

( * ) Notice: Subject to any disclaimer, the term of this patent is extended or adjusted under 35 U.S.C. 154(b) by 10 days.

(21) Appl. No.: 14/671,461

(22) Filed: Mar. 27, 2015

(65) Prior Publication Data

US 2015/0273128 A1    Oct. 1, 2015

Related U.S. Application Data

(60) Provisional application No. 61/972,055, filed on Mar. 28, 2014.

(51) Int. Cl.
| | | |
|---|---|---|
| A61M 1/36 | (2006.01) | |
| A61M 1/38 | (2006.01) | |
| B04B 5/04 | (2006.01) | |
| B04B 13/00 | (2006.01) | |

(52) U.S. Cl.
CPC ........ *A61M 1/3693* (2013.01); *A61M 1/3696* (2014.02); *A61M 1/382* (2013.01); *B04B 5/0442* (2013.01); *B04B 13/00* (2013.01); *A61M 2205/3306* (2013.01); *B04B 2013/006* (2013.01)

(58) Field of Classification Search
CPC . B04B 11/02; B04B 2013/006; B04B 5/0442; B04B 13/00; A61M 1/3693; A61M 1/382; A61M 1/3696; A61M 2205/3306

USPC .................................................. 210/739, 787
See application file for complete search history.

(56) References Cited

U.S. PATENT DOCUMENTS

| | | | |
|---|---|---|---|
| 4,151,844 | A | 5/1979 | Cullis et al. |
| 4,493,691 | A | 1/1985 | Calari |
| 4,557,719 | A | 12/1985 | Neumann et al. |
| 4,670,002 | A | 6/1987 | Koreeda et al. |

(Continued)

FOREIGN PATENT DOCUMENTS

| | | |
|---|---|---|
| DE | 3413065 A1 | 10/1984 |
| EP | 0392475 A2 | 10/1990 |

(Continued)

OTHER PUBLICATIONS

International Search Report and Written Opinion, PCT/US2015/023095, dated Jul. 28, 2015.

(Continued)

*Primary Examiner* — David C Mellon
*Assistant Examiner* — Liam Royce
(74) *Attorney, Agent, or Firm* — Terumo BCT, Inc. IP Law Department

(57) ABSTRACT

Embodiments are described for receiving first data related to an amount of a first component in a multi-component liquid. A gain may be determined based on the first data. The multi-component liquid may be separated into at least two components. The gain may then be used to control a position of an interface between two separated components of the multi-component liquid, such as by using the gain in changing a speed of a pump pumping at least one of the components.

19 Claims, 13 Drawing Sheets

(56) References Cited

U.S. PATENT DOCUMENTS

| | | | |
|---|---|---|---|
| 4,724,317 A | 2/1988 | Brown et al. | |
| 4,834,707 A * | 5/1989 | Evans | A61B 17/3417 |
| | | | 604/122 |
| 4,834,890 A | 5/1989 | Brown et al. | |
| 5,076,911 A | 12/1991 | Brown et al. | |
| 5,104,526 A | 4/1992 | Brown et al. | |
| 5,260,598 A | 11/1993 | Brass et al. | |
| 5,282,982 A | 2/1994 | Wells | |
| 5,316,667 A | 5/1994 | Brown et al. | |
| 5,322,620 A | 6/1994 | Brown et al. | |
| 5,414,778 A | 5/1995 | Schwartz et al. | |
| 5,653,887 A | 8/1997 | Wahl et al. | |
| 5,658,240 A * | 8/1997 | Urdahl | A61M 1/02 |
| | | | 604/6.01 |
| 5,741,213 A | 4/1998 | Kouchi et al. | |
| 5,958,250 A | 9/1999 | Brown et al. | |
| 5,980,757 A | 11/1999 | Brown et al. | |
| 5,984,892 A * | 11/1999 | Bedingham | A61M 1/0031 |
| | | | 128/DIG. 13 |
| 6,026,174 A | 2/2000 | Palcic et al. | |
| 6,053,856 A | 4/2000 | Hlavinka | |
| 6,078,680 A | 6/2000 | Yoshida et al. | |
| 6,334,842 B1 | 1/2002 | Hlavinka et al. | |
| 6,358,409 B1 * | 3/2002 | Jacoby, Jr. | B01D 17/0214 |
| | | | 210/122 |
| 6,506,606 B1 | 1/2003 | Winkelman et al. | |
| 6,514,189 B1 | 2/2003 | Hlavinka et al. | |
| 6,707,952 B1 | 3/2004 | Tan et al. | |
| 6,790,371 B2 | 9/2004 | Dolecek | |
| 7,029,430 B2 | 4/2006 | Hlavinka et al. | |
| 7,327,443 B2 | 2/2008 | Scibona et al. | |
| 7,355,685 B2 | 4/2008 | Scibona et al. | |
| 7,422,693 B2 | 9/2008 | Carter et al. | |
| 7,605,388 B2 | 10/2009 | Carter et al. | |
| 7,906,771 B2 | 3/2011 | Carter et al. | |
| 7,943,916 B2 | 5/2011 | Carter et al. | |
| 8,609,339 B2 * | 12/2013 | Suo | C12Q 1/6806 |
| | | | 435/6.12 |
| 2002/0031255 A1 | 3/2002 | Kasdan et al. | |
| 2002/0148787 A1 | 10/2002 | Dolecek et al. | |
| 2003/0036751 A1 | 2/2003 | Anderson et al. | |
| 2004/0153128 A1 | 8/2004 | Suresh et al. | |
| 2005/0051466 A1 | 3/2005 | Carter et al. | |
| 2007/0085996 A1 | 4/2007 | Mangan et al. | |
| 2008/0041772 A1 | 2/2008 | Sweat et al. | |
| 2008/0283781 A1 * | 11/2008 | Carter | B04B 13/00 |
| | | | 250/573 |
| 2011/0269614 A1 | 11/2011 | Lindner et al. | |

FOREIGN PATENT DOCUMENTS

| | | |
|---|---|---|
| EP | 1146748 B1 | 10/2001 |
| JP | H01216242 A1 | 8/1989 |
| WO | 9908091 A1 | 2/1999 |
| WO | 2002013139 A1 | 2/2002 |
| WO | 2006071302 A2 | 7/2006 |
| WO | 2008021633 A2 | 2/2008 |

OTHER PUBLICATIONS

Perona et al, Scale-Space and Edge Detection Using Anisotropic Diffusion, IEEE Transactions on Pattern Analysis and Machine Intelligence, 1990 v. 12, No. 7, pp. 629-639.

Salgaller, Michael L., "A Manifesto on the Current State of Dendritic Cells in Adoptive Immunotherapy", Transfusion, 2003, 48:422-424.

* cited by examiner

GAIN IN SEPARATION PROCESSES WITH CONTROL LOOP

CROSS-REFERENCE TO RELATED PATENT APPLICATIONS

This application claims priority to U.S. Provisional Patent Application No. 61/972,055, filed Mar. 28, 2014, and entitled GAIN IN SEPARATION PROCESSES WITH CONTROL LOOP, which is hereby incorporated by reference in its entirety as if set forth herein in full.

BACKGROUND

Separation processes are commonly used to isolate components of multi-component liquids in a variety of technology areas. For example, in mining operations, separation processes may be used to separate multi-component liquids into components, e.g., slurries of ore into solid and liquid components. Separation processes are also common in medicine. Blood components are often separated from whole blood for transfusion or therapeutic purposes. Apheresis is one example of a blood separation process in which components are separated from whole blood.

In some separation processes, the purity of the components being separated from a multi-component liquid may be important. For example, some apheresis processes are performed to collect a particular target component from blood, e.g., mononuclear cells, for therapeutic reasons. In these separation processes it may be important to collect as much of the target component as possible with as little of the other components as possible. Providing mechanisms in the separation process to control the purity of a target component being collected may be useful.

Embodiments of the present invention have been made in light of these and other considerations. However, the problems discussed above do not limit the applicability of the embodiments of the present invention to other applications.

SUMMARY

The summary is provided to introduce aspects of some embodiments of the present invention in a simplified form, and is not intended to identify key or essential elements of the claimed invention, nor is it intended to limit the scope of the claims.

Embodiments of the present invention relate to processes and systems for determining a gain for use in a control loop of a separation process and using the gain during the separation process. Embodiments provide for receiving first data related to an amount of a first component in a multi-component liquid. The multi-component liquid may be separated into at least two components. A gain may be determined based on the first data. The gain may then be used to control a position of an interface between two separated components of the multi-component liquid. Components of the multi-component liquid may then be collected after separation. Embodiments may additionally involve receiving data regarding the position of the interface and using the determined gain to change the position of the interface. Other embodiments may involve determining a metric based on the first data and selecting a gain based on the metric.

BRIEF DESCRIPTION OF THE DRAWINGS

Non-limiting and non-exhaustive embodiments are described with reference to the following figures.

DETAILED DESCRIPTION

Figure 1:
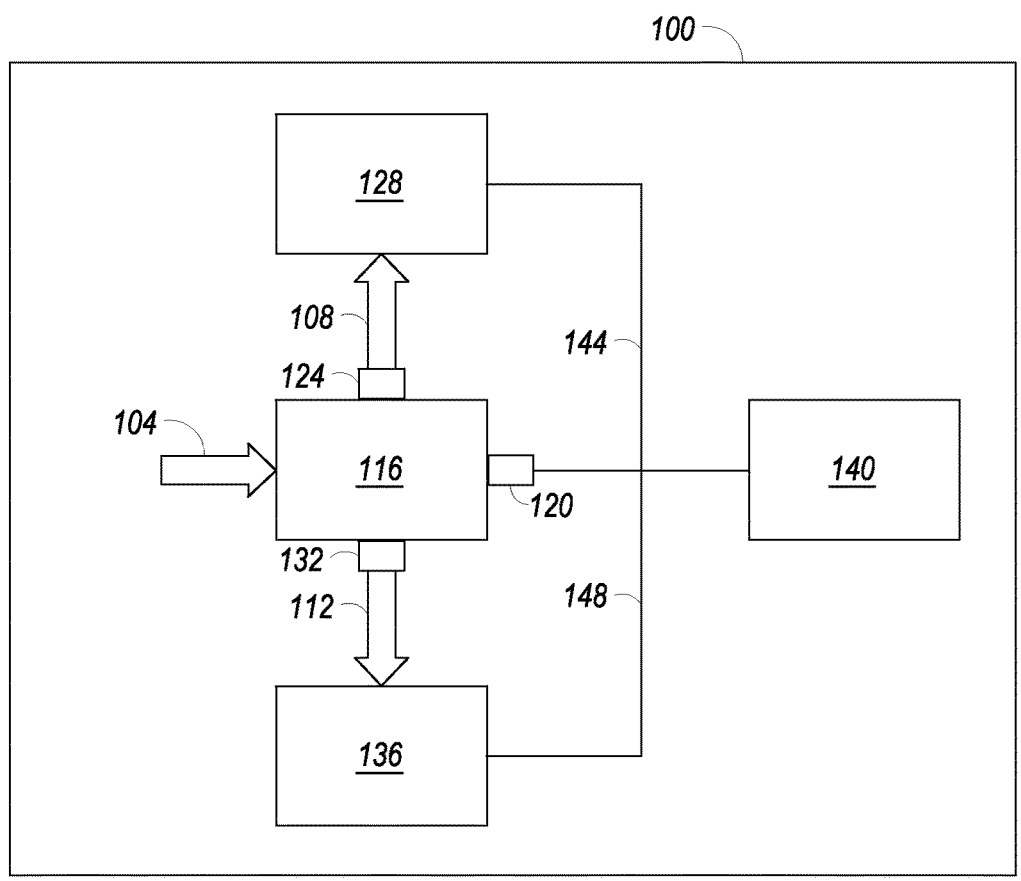
FIG. 1 illustrates a block diagram of a system for separating a multi-component liquid into at least two components consistent with an embodiment of the present invention.

The principles of the present invention may be further understood by reference to the following detailed description and the embodiments depicted in the accompanying drawings. It should be understood that although specific features are shown and described below with respect to detailed embodiments, the present invention is not limited to the embodiments described below.

Reference will now be made in detail to the embodiments illustrated in the accompanying drawings. Wherever possible, the same reference numbers are used in the drawings and the description to refer to the same or like parts.

FIG. 1 illustrates a block diagram of a separation system 100 that may be used with, or may implement, embodiments of the present invention. The separation system 100 may be used to take a multi-component liquid 104 and separate the multi-component liquid 104 into at least two components 108 and 112. Separation system 100 may additionally include: a separator 116 that separates the multi-component liquid 104, a module 120 for receiving data regarding at least one component of the liquid, pump 124 for pumping component 108 into container 128, and a pump 132 for pumping component 112 into container 136.

System 100 also includes a processor 140, which is connected to pump 124, pump 132, and module 120. In addition, system 100 includes control loops 144 and 148 that allow processor 140 to control pump 124 and pump 132 and consequently the collection of the component 108 and component 112. As described in greater detail below, processor 140 may receive data from module 120 regarding the separation of multi-component liquid 104, and in response adjust the speed of pump 124 and/or pump 132.

Although module 120 is illustrated in FIG. 1 as a single block, in embodiments, module 120 may include a number of different hardware and/or software systems for receiving data and sending data to processor 140. For example, module 120 may include in embodiments one or more of a data receiving system (e.g., an imaging system); a user interface (e.g., a display, a keyboard, touch sensitive hardware); processor(s); memory devices; and/or software modules.

In embodiments, module 120 may include hardware and/or software that receives first data regarding an amount of a component in the multi-component liquid 104, and also receives second data regarding separation and/or collection of a component of the multi-component liquid 104. The first and second data may then be sent to processor 140. Processor 140 may then adjust the speed of pump 124 or pump 132 depending on the data.

In one embodiment, module 120 may include a user interface that allows an operator of system 100 to enter first data. The first data may be a concentration of one component in the multi-component liquid 104. In other embodiments, module 120 may include a data receiving system that generates first data indicating a concentration of one or more components in the multi-component liquid 104. As described in greater detail below, the first data may be used to set a control gain for control loops 144 and/or 148.

In addition, module 120 may also generate second data regarding the separation of the multi-component liquid 104. This second data may indicate a variety of different conditions, non-limiting examples including, whether multi-component liquid 104 is being properly separated (e.g., whether components are well separated into distinct layers), or the location of an interface between two components that have been separated. As noted below, the second data may be used to adjust pump speeds of pump 124 and/or pump 132. The adjustment of the pumps (124, 132) may also utilize the control gain determined from the first data.

In embodiments, system 100 may operate as follows. First data, regarding a concentration of one component in the multi-component liquid 104 may be received by processor 140 for example from module 120. As noted above, the first data may originate from an operator, or from a system such as module 120. The first data may then be used to determine a control gain for the control loop 144 and/or control loop 148. In embodiments, the control gain is used when changing speeds of the pumps (124, 132).

As may be appreciated, the control gain used for the control loops (144, 148) may affect the separation of the multi-component liquid. If the control gain is high, then when the speed of a pump is changed, the change may occur rapidly. If the control gain is low, the pump may change speeds more slowly. If there is a low concentration of a first component in the multi-component liquid, changing the pump speed quickly may cause a second (different) component to be swept into the collection of the first component. In other words, the quick change in speed may cause other components to be collected with the first component, reducing the purity of the first component. However, in embodiments where there is a high concentration of the first component, a high control gain, which causes the pump speed to change more rapidly, may be useful in collecting the first component.

Figure 2:
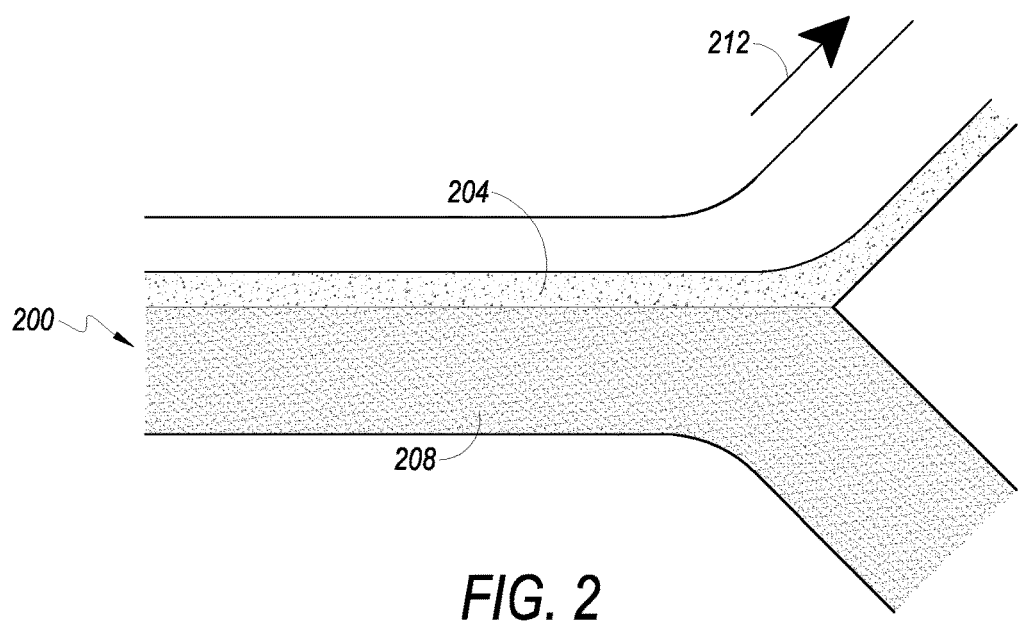
FIGS. 2-5 illustrate embodiments of using high control gain or low control gain in a process of collecting components separated from a multi-component liquid.
Figure 3:
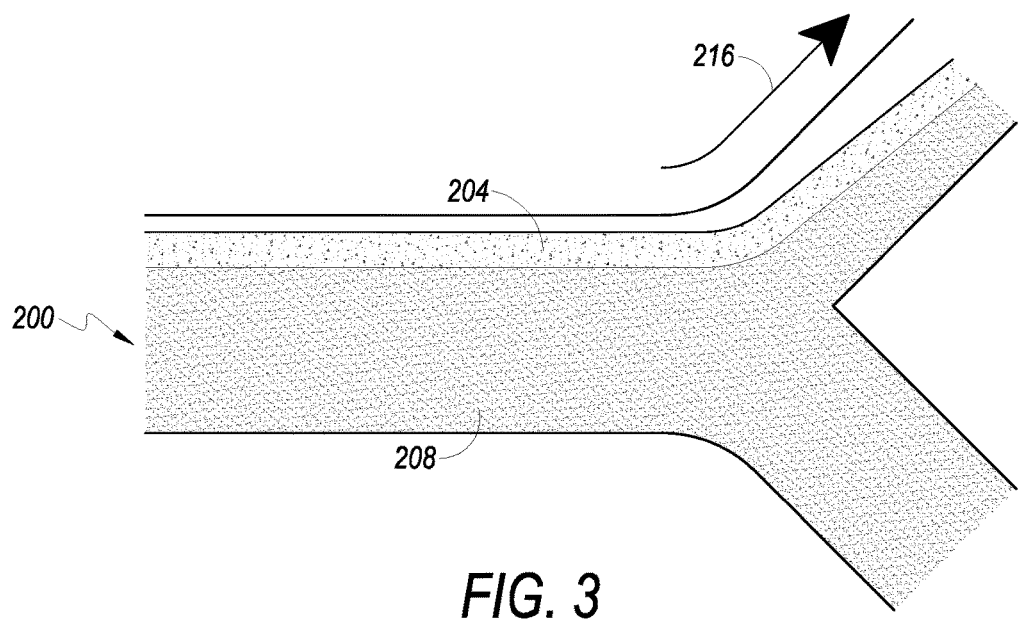

FIGS. 2-5 illustrate embodiments of using high control gain or low control gain in a separation process. FIGS. 2 and 3 illustrate a multi-component liquid 200 with a first component 204 of relatively low concentration and a second component 208 of higher concentration. FIGS. 2 and 3 illustrate the components after they have been separated, with a layer of first component 204 above a layer of the second component 208. Arrow 212 in FIG. 2 illustrates a rate at which the first component is being pumped in this case a relatively low rate. FIG. 3 illustrates a situation in which the rate at which the first component is being pumped (as illustrated by arrow 216) is increased quickly. That is, a pump that is pumping component 204 may be controlled by a control loop with a high gain, causing pump speeds to change quickly. As shown in FIG. 3, the quick change causes some of the second component 208 to be swept with component 204.

Figure 4:
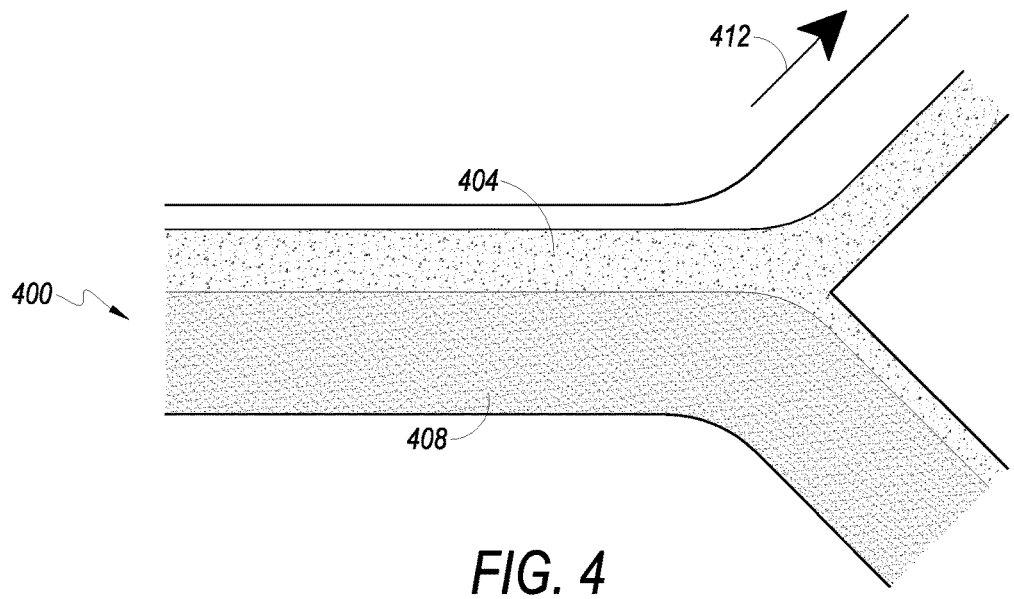
Figure 5:
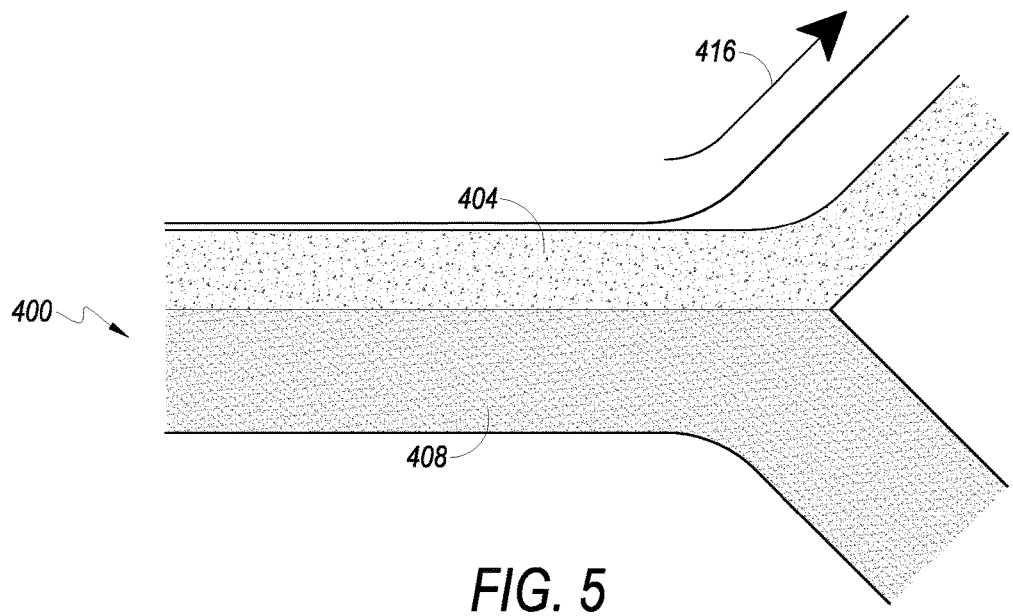

FIGS. 4 and 5 illustrate a multi-component liquid 400 with a first component 404 and a second component 408. As illustrated in FIGS. 4 and 5, first component 404 is of greater concentration than first component 204 in multi-component liquid 200 (FIGS. 2 and 3). FIGS. 4 and 5 illustrate the components after they have been separated, with a layer of first component 404 above a layer of the second component 408. Arrow 412 in FIG. 4 illustrates a rate at which the first component 404 is being pumped (at a relatively slow rate). FIG. 5 illustrates a situation in which the rate at which the first component 404 is being pumped (as illustrated by arrow 416) is increased quickly. That is, a pump that is pumping component 404 may be controlled by a control loop with a high gain, causing pump speeds to change quickly. As shown in FIG. 5, the quick change causes more of the first component 404 to be collected, without sweeping up any, or much, of the second component 408.

FIGS. 2-5 are merely one example of how a control gain may affect the collection of a component being separated from a multi-component liquid. FIGS. 2-5 also illustrate how a concentration of a component may affect the selection of an appropriate gain, consistent with embodiments of the present invention.

Referring back to operation of system 100 (FIG. 1), the multi-component liquid 104 that may include a number of components is introduced into separator 116 as noted above. The separator 116 separates the multi-component liquid 104 into at least two components, such as component 108 and 112. After separation, component 108 is pumped by pump 124 into container 128 where the component 112 is collected. Component 112 is pumped by pump 132 into container 136 where the component 108 is collected. During the collection, module 120 may receive second data that may be used by processor 140 to change the speed of one or more of pumps 124 and/or 132 through control loops 144 and 148, respectively. As may be appreciated, the change of the pump speed will reflect the previously determined control gain. The second data may be information indicating whether collection of the components 108 and 112 is being done efficiently, the location of an interface between components, or other information.

It is noted that system 100 may be used to separate any component from any multi-component stream. The use of a concentration to determine a control loop gain may be applied, in embodiments, to any separation process that includes a control loop, such as any separation process that includes a pump control loop.

As noted above, embodiments are directed to methods, systems, and devices that may be used to separate any multi-component stream into one or more components. The embodiments in FIGS. 6-11 are described below with respect to separation of whole blood, or a component of whole blood, into blood components. It is noted that the description is provided merely for illustrative purposes, and although embodiments may be used in the separation of blood into blood components, the present invention is not limited thereto.

Figure 6:
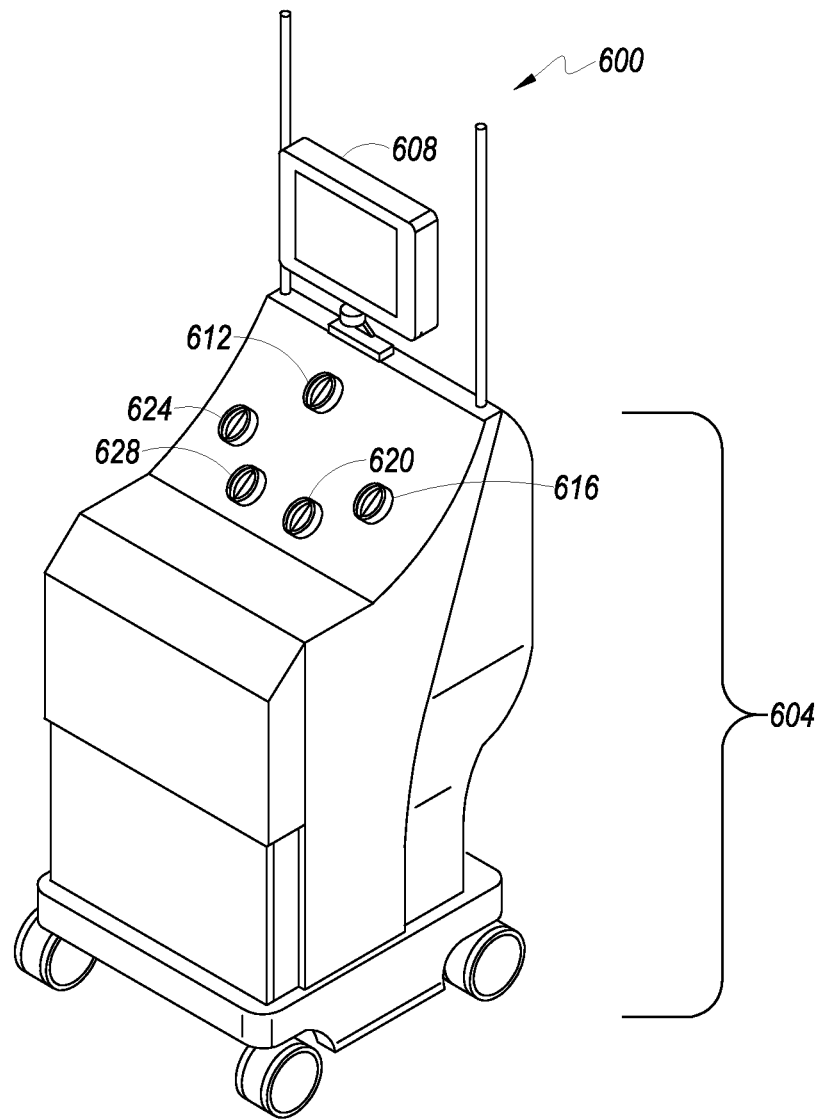
FIG. 6 illustrates a perspective view of a separator that may be used to separate a multi-component liquid (e.g., whole blood) into components consistent with an embodiment.

FIG. 6 illustrates a perspective view of a system 600 that may be used to separate whole blood (or blood components) into components consistent with an embodiment of the present invention. System 600 includes a housing 604 where a number of devices that are part of system 600 may be housed. For example, housing 604 may house a blood separation system and one or more computer systems. In embodiments, user interface 608 may communicate with the one or more computer systems to receive and provide data to an operator of system 600. Additionally, system 600 includes a number of pumps (612, 616, 620, 624, 628) used to pump blood and blood components before and after separation. In embodiments, the pumps may be partially housed in housing 604. In embodiments, system 600 may be a SPECTRA OPTIA® system, manufactured by Terumo BCT, Inc., of Lakewood, Colo.

Figure 7:
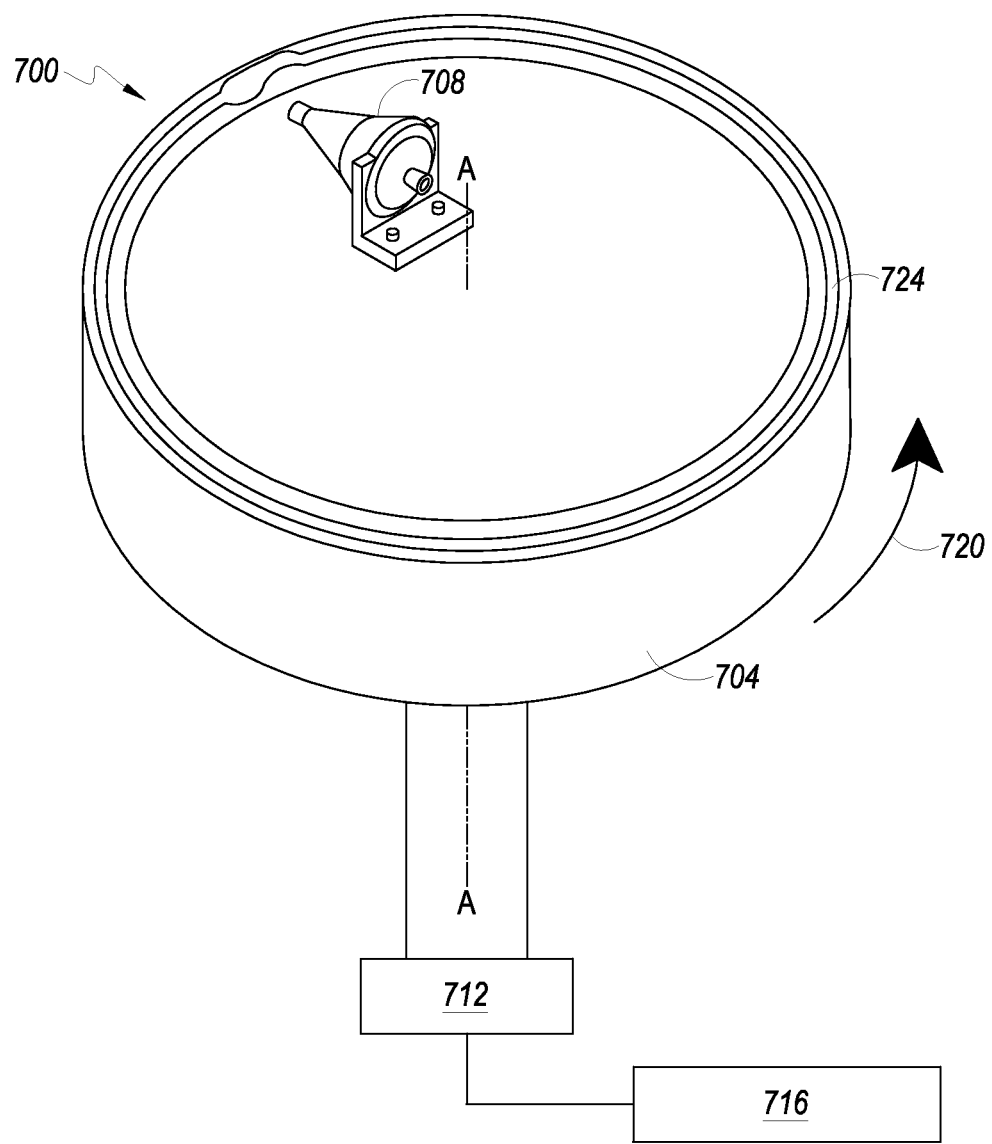
FIG. 7 illustrates a perspective view of a centrifuge and separation chamber that may be used in a separator for separating components of a multi-component liquid (e.g., whole blood) consistent with an embodiment of the present invention.

FIG. 7 illustrates a perspective view of a separation system 700 that may be used to separate blood into components and may be used in system 600. Separation system 700 includes a centrifuge 704 and a separation chamber 708. Centrifuge 704 may be connected to a motor 712 that spins the centrifuge 704 at very high RPMs. Controller 716 may be connected to motor 712 and be used to control the speed at which motor 712 spins centrifuge 704. In an embodiment, the centrifuge 704 spins in the direction of arrow 720. As centrifuge 704 spins, liquid, such as whole blood, within channel 724, separating the liquid into components. In some embodiments, one component separated in channel 724 is further separated in chamber 708 into additional components. For example, a buffy coat (combination of white blood cells and platelets) may be separated into white blood cells and platelets in chamber 708. It is noted, that chamber 708 is shown and described for completeness, but it is not always used in embodiments of the present invention. For example, embodiments may be implemented in protocols that do not utilize a separation chamber such as chamber 708.

Figure 8:
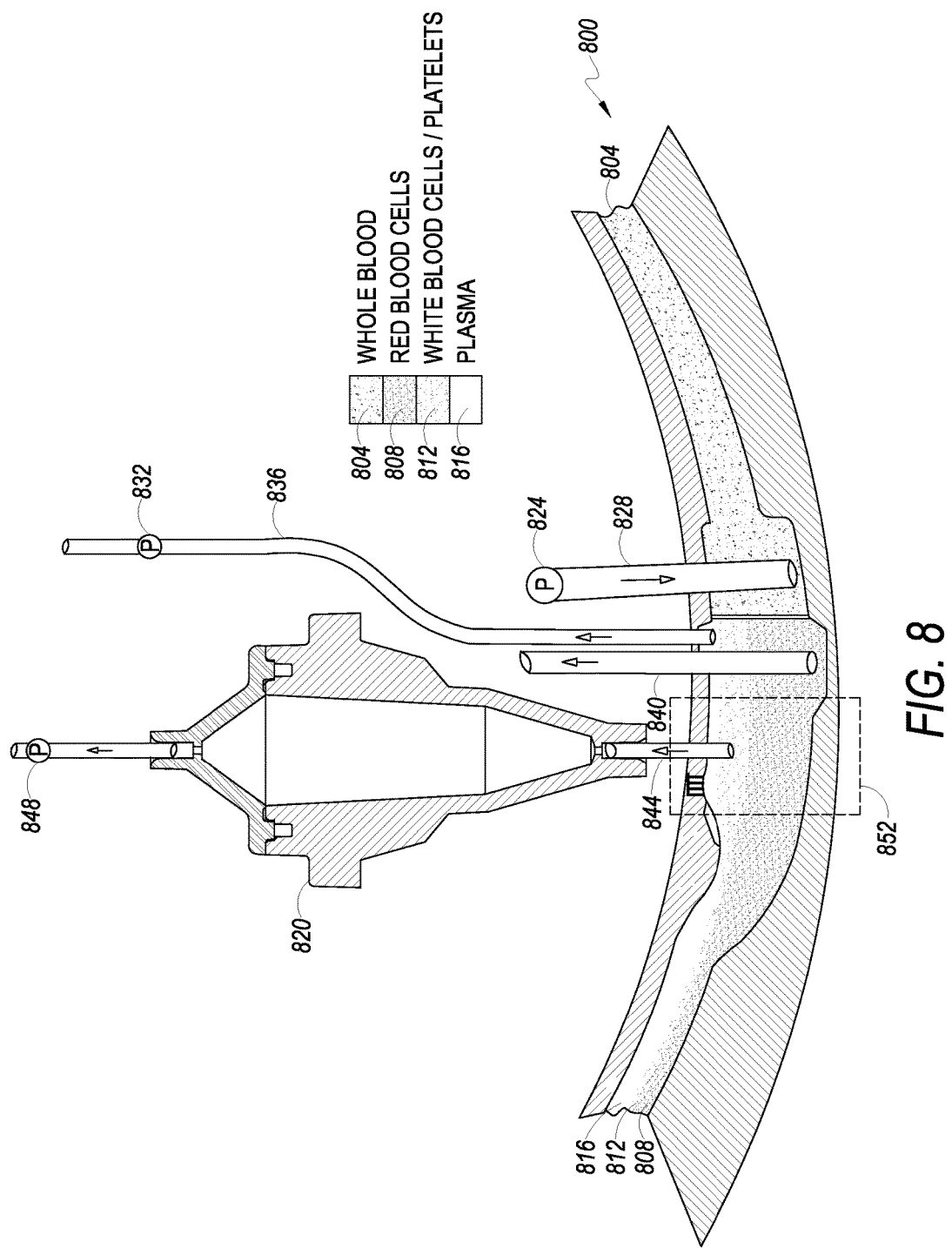
FIG. 8 illustrates a cross-sectional view of a centrifuge, and separation chamber, separating components from whole blood consistent with an embodiment.

FIG. 8 illustrates a cross-sectional, partial view of one embodiment of a separation channel 800 of a centrifuge, and separation chamber 804, where components are being separated from whole blood, consistent with an embodiment of the present invention. In the embodiment shown in FIG. 8, whole blood 804 is being separated into components that include red blood cells 808, a buffy coat 812 (containing platelets and white blood cells), and plasma 816. The platelets are further separated from the white blood cells in chamber 820. In other embodiments, chamber 820 may not be used and instead the components will be collected after the first separation.

As shown in FIG. 8, pump 824 pumps whole blood 804 into channel 800 through conduit 828. Channel 800, in embodiments, may be positioned around a centrifuge (e.g., centrifuge 704) that spins and separates the whole blood 804 into components. On the left side of FIG. 8, whole blood 804 is shown as separated into red blood cells 808, white blood cells/platelets 812, and plasma 816.

Pump 832 removes the separated plasma 816 through conduit 836, which has an inlet toward a top of channel 800. Conduit 840 has an inlet toward a bottom of channel 800, which allows red blood cells 808 to be removed from channel 800. Finally, conduit 844 is used to remove white blood cells/platelets 812 from channel 800 and into chamber 820, where the platelets are separated from the white blood cells. A pump 848 may be used to remove white blood cells and platelets from chamber 820 after separation.

Figure 9:
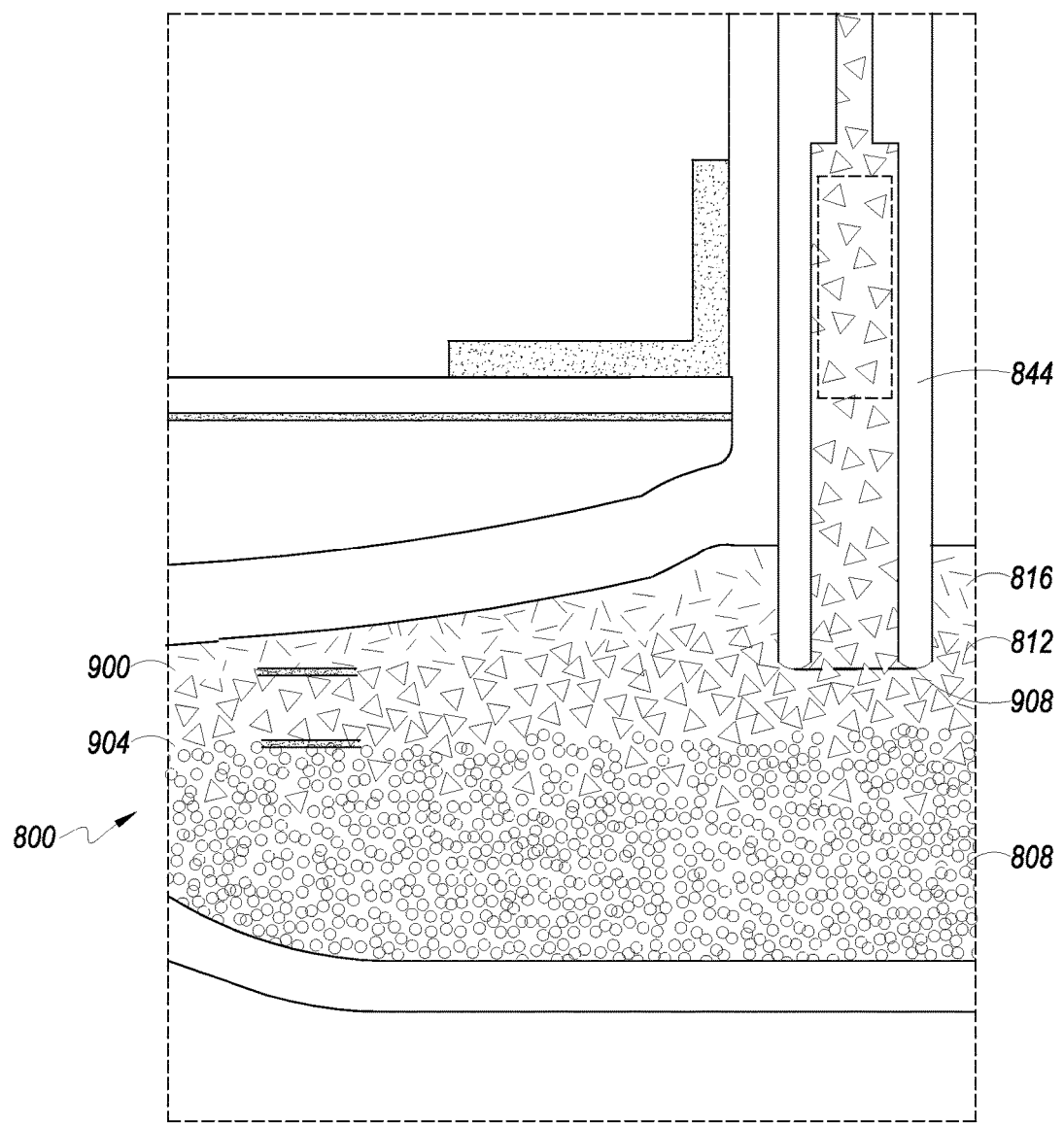
FIG. 9 illustrates a zoomed in portion of FIG. 8 showing an interface between components of whole blood after separation of the components.

FIG. 9 illustrates a magnified view of section 852 shown in FIG. 8 magnified to better show the various components separated from the whole blood 804 and the interface(s) between the separated components. As shown in FIG. 9, after separation of the whole blood 804 into components, interfaces 900 and 904 are formed. Interface 900 is formed between plasma 816 and white blood cells/platelets 812, while interface 904 is formed between white blood cells/platelets 812 and red blood cells 808.

FIG. 9 illustrates the inlet 908 of conduit 844 which is used to remove white blood cells/platelets 812 from channel 800. In order to collect white blood cells/platelets 812, inlet 908 should be positioned between interfaces 900 and 904. If inlet 908 is above interface 900, plasma 816 will be collected. If inlet 908 is below interface 904, red blood cells 808 will be collected. Accordingly, to maintain collection of white blood cells/platelets 812 with as little other components as possible, inlet 908 should be positioned between interface 900 and 904 as much as possible during the collection process.

As can be appreciated, the position of the interfaces 900 and 904 may change, depending on a number of factors, non-limiting examples including the concentration of the components in the whole blood 804 (e.g., more red blood cells may raise the level of the interfaces 900 and 904) or the speed at which pumps may be drawing out components from channel 800 (e.g, lower pump speeds may lower the level of the interfaces 900 and 904). Accordingly, embodiments may be implemented as part of feedback loops that control the level of interfaces 900 and 904 in order to collect one or more components, e.g. white blood cells/platelets.

Figure 10:
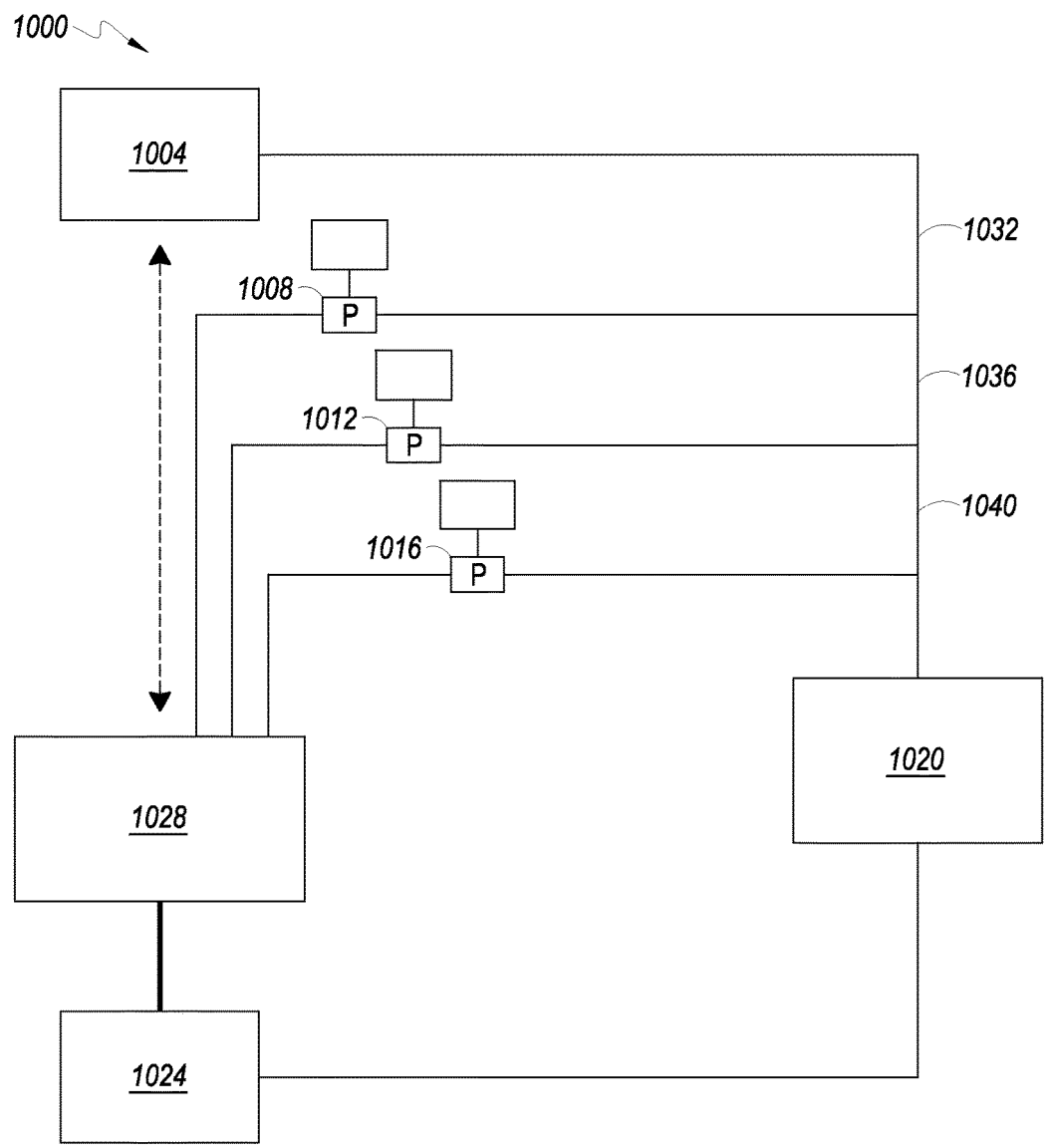
FIG. 10 illustrates a block diagram of a separation system with a data receiving system, pumps, and control loops for separating and collecting components separated from a multi-component liquid (e.g., whole blood) consistent with embodiments.

FIG. 10 illustrates a block diagram of a separation system 1000 with a data receiving system 1004, pumps (1008, 1012, 1016), a processor 1020, control loop 1032 (including data receiving system 1004, pump 1008 and processor 1020), control loop 1036 (including data receiving system 1004, pump 1012 and processor 1020), and control loop 1040 (including data receiving system 1004, pump 1016 and processor 1020). Processor 1020, among other functions, receives data from the data receiving system 1004, controls operation/speed of the pumps (1008, 1012, 1016), and controls operation/speed of motor 1024, which spins a centrifuge 1028. In embodiments, system 1000 may be implemented as part of system 600 in FIG. 6 and used to separate blood into blood components.

In operation, whole blood may be introduced into a channel in centrifuge 1028. Motor 1024, under control of processor 1020, spins centrifuge 1028 and separates whole blood into components. In embodiments, pump 1008 may pump plasma from the channel, while pump 1012 may pump white blood cells/platelets, and pump 1016 may pump red blood cells.

In embodiments, during separation of whole blood into components, data receiving system 1004 receives data regarding interfaces between components; see e.g., interfaces 900 and 904 (FIG. 9). The data is transmitted to processor 1020 as part of feedback control loops 1032, 1036, and 1040. In response to the data, processor 1020 may change the speed of one or more of the pumps 1008, 1012, and/or 1016. For example, as noted above with respect to FIG. 9, if an inlet of a collection tube (e.g., collecting white blood cells/platelets) is above an interface between the plasma and the white blood cells/platelets, the processor 1020 may speed up pump 1008 to pump plasma more quickly and raise the interface so that the inlet is below the interface. As another example, the speed of pump 1016 may be increased by processor 1020 to remove red blood cells from the channel and lower the interface.

In embodiments, processor 1020 also receives data regarding the concentration of one of the components in the whole blood, e.g., platelets. Processor 1020 in embodiments receives this information prior to receiving interface data from receiving system 1004, as described above. Processor 1020 may then utilize the data regarding concentration to select a control gain to use when it changes the speed of pumps (1008, 1012, and 1016). In some embodiments, the concentration of one of the components may be input by an operator. Alternatively, the data receiving system 1004 may receive data that is indicative of the concentration of one of the components.

In some embodiments, system 1000 may perform an interface set up procedure, which establishes and recognizes interfaces between the separated components; see e.g., interfaces 900 and 904 (FIG. 9). As part of the interface set up procedure, data receiving system 1004 collects data that may indicate the position of the interfaces and the amount of one or more of the components being separated. The data may then be used by processor 1020 to determine a control gain to use when adjusting the speed of pumps (1008, 1012, and 1016).

In embodiments, the data receiving system 1004 may generate data by detecting light that is transmitted or reflected by the whole blood and/or its components. In one embodiment, the data generated by data receiving system 1004 may be entered into a mathematical function to generate a metric. The metric may then be correlated to a previously established control gain.

It is noted that in embodiments, data receiving system 1004 may utilize different mechanisms, components, or systems, for capturing data regarding the multi-component liquid or components in the liquid, e.g., concentration of components in a multi-component liquid such as whole blood, or information regarding the interfaces between separated components. In embodiments, data receiving system 1004 may include one or more light sources and one or more light detectors. The light source(s) (e.g., LED's) may be positioned so that light is directed at the whole blood or the components in whole blood after separation. The detector(s) may then be positioned to detect the amount of light that is transmitted, reflected, or both transmitted and reflected. This received light intensity data may indicate a variety of different conditions, non-limiting examples including, whether the whole blood is being properly separated or the location of an interface between two components that have been separated. The data may also be correlated to component concentrations. In some embodiments, data receiving system 1004 may be an optical system such as imaging system 1100 described with respect to FIG. 11 below.

Figure 11:
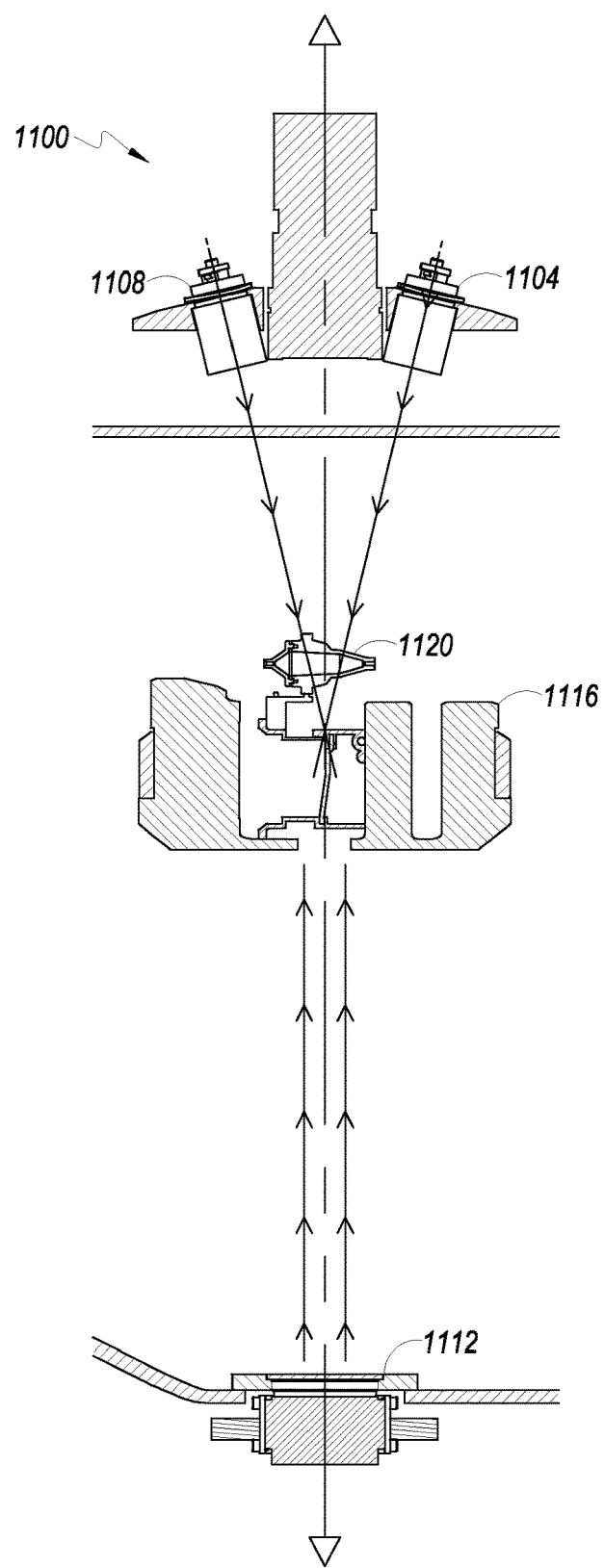
FIG. 11 illustrates an embodiment of an imaging system that may be used as a data receiving system in a control loop consistent with one embodiment of the present invention.

FIG. 11 illustrates imaging system 1100 that may be used as part of a data receiving system 1004 in system 1000 (FIG. 10), utilized in system 600 (FIG. 6), or used as part of module 120 (FIG. 1) consistent with embodiments. In the embodiment shown in FIG. 11, imaging system 1100 includes camera 1104, camera 1108, and camera 1112. In operation, centrifuge 1116 separates whole blood into plasma, white blood cells/platelets, and red blood cells. White blood cells/platelets are further separated in chamber 1120.

In embodiments, camera 1104 and camera 1108 are directed at chamber 1120 and capture image data of white blood cells/platelets as they are being separated in chamber 1120. Camera 1112 captures image data of components as they are separated from whole blood in centrifuge 1116 and/or image data showing an interface between separated components and the location of the interface in relation to a collection tube. The cameras may be connected to a processor, such as processor 1020, which may use the image data generated by the cameras to control pumps or a motor spinning centrifuge 1116 using control loops such as control loops 1032, 1036, and 1038. In some embodiments, module 120 (FIG. 1) and/or data receiving system (FIG. 10) may incorporate one or more features of imaging system 1100.

The imagining system 1100, as depicted in FIG. 11, is provided merely for illustrated purposes and is not intended to limit the present invention. Other imaging systems with additional cameras, detectors, light sources, and/or optics may be used. Furthermore, imaging system 1100 may have cameras positioned in different locations than shown in FIG. 11. For example, in embodiments, one of cameras 1104, 1108, or 1112 may be positioned on a plane that is substantially parallel to a plane on which centrifuge 1116 is positioned. As another example, in some embodiments, a separation chamber may not be used, in which case the cameras 1104 and camera 1108 will be directed to other locations where separation of components may be occurring.

It is noted that in some embodiments, a separation system may incorporate one or more of the features described above with respect to FIGS. 6-11. For example, separation system 600 may include a separation system 1000 and imaging system 1100. In other embodiments, only some features described above may be incorporated and combined with other features. Therefore, the present invention is not limited to any specific combination of features described above with respect to FIGS. 6-11, which are provided merely for illustrative purposes.

Figure 12:
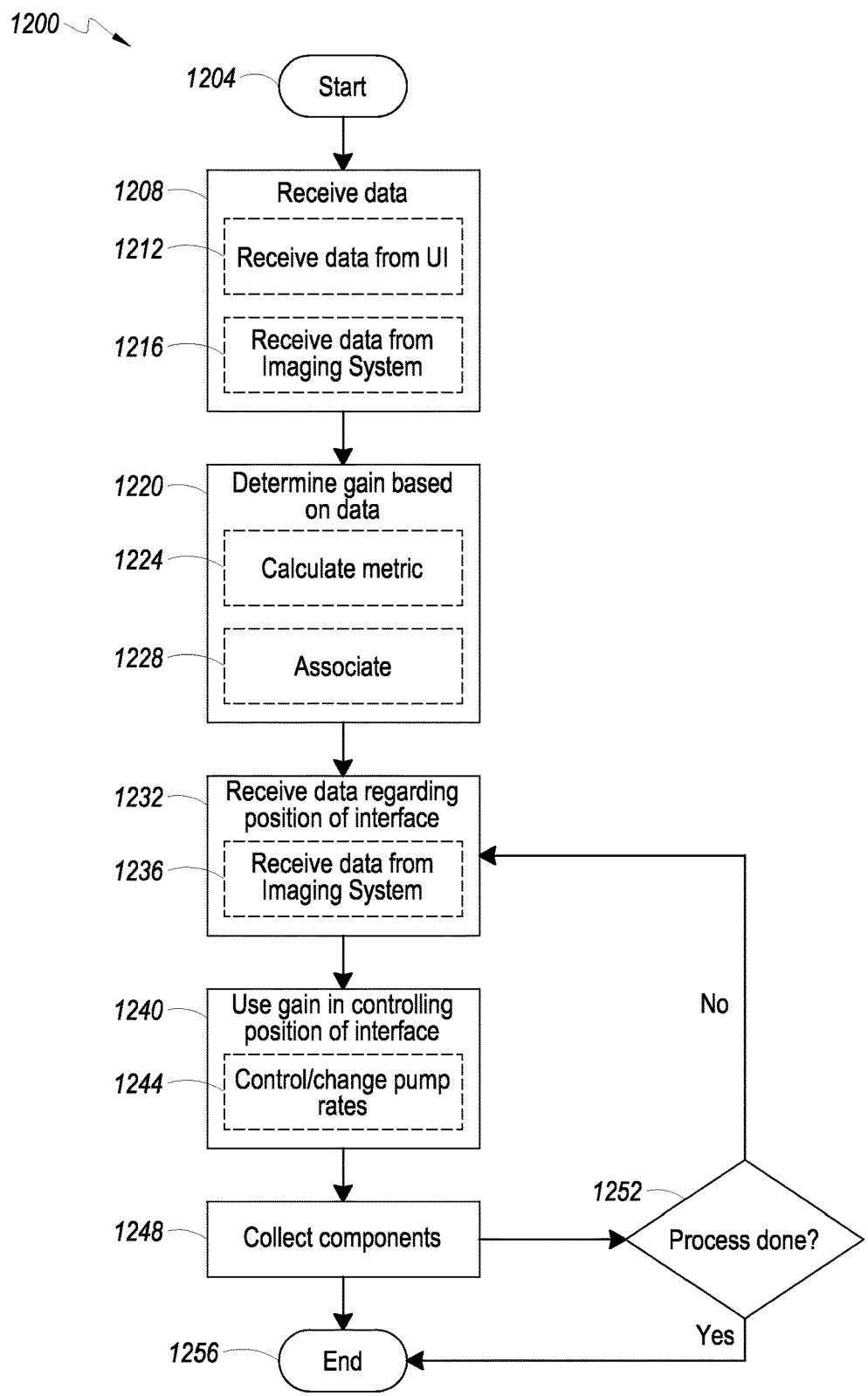
FIG. 12 illustrates a flow diagram of a process for consistent with an embodiment of the present invention.

FIG. 12 illustrates flow chart 1200 that may be performed in embodiments of the present invention. Although specific devices may be described below for performing steps in flow chart 1200, the present invention is not limited thereto. For example, some steps may be described as performed by a processor, such as processor 140 or processor 1020. This is done merely for illustrative purposes, and flow chart 1200 is not limited to being performed by any specific device.

Flow chart 1200 illustrates a process consistent with an embodiment of the present invention. In embodiments, flow chart 1200 may be implemented by a separation system such as system 100 (FIG. 1), system 600 (FIG. 6), and/or system 1000 (FIG. 10).

Flow chart 1200 starts at 1204. Flow passes from 1204 to step 1208, where first data may be received. The first data may be data indicating a concentration of components in the multi-component liquid. In embodiments, step 1208 may involve some optional sub-steps. For example, in one embodiment, an operator may input a concentration into a user interface (UI) at sub-step 1212, such as user interface 608 (FIG. 6). As one example, if the multi-component liquid that will be separated into components is whole blood, the data input at step 1208 may be a concentration of a blood component. The concentration may be determined by an operator performing tests or some analysis on samples of the whole blood to determine a concentration. In one embodiment involving whole blood, the data may be a concentration of platelets.

In other embodiments, the data received at step 1208 may be received from an imaging system such as system 1100. For example, the data may be image data taken by one or more cameras. In this embodiment, at sub-step 1216, data from an imaging system would be received. In other embodiments, the data may be received from a light detector that detects light transmitted or reflected by the multi-component liquid and/or the separated components.

After step 1208, flow passes to step 1220, where, based on the data received at step 1208, a determination is made as to the gain to be used when changing speed of a pump pumping the multi-component liquid (or a separated component of the multi-component liquid). Step 1220 may also involve a number of sub-steps.

Figure 13:
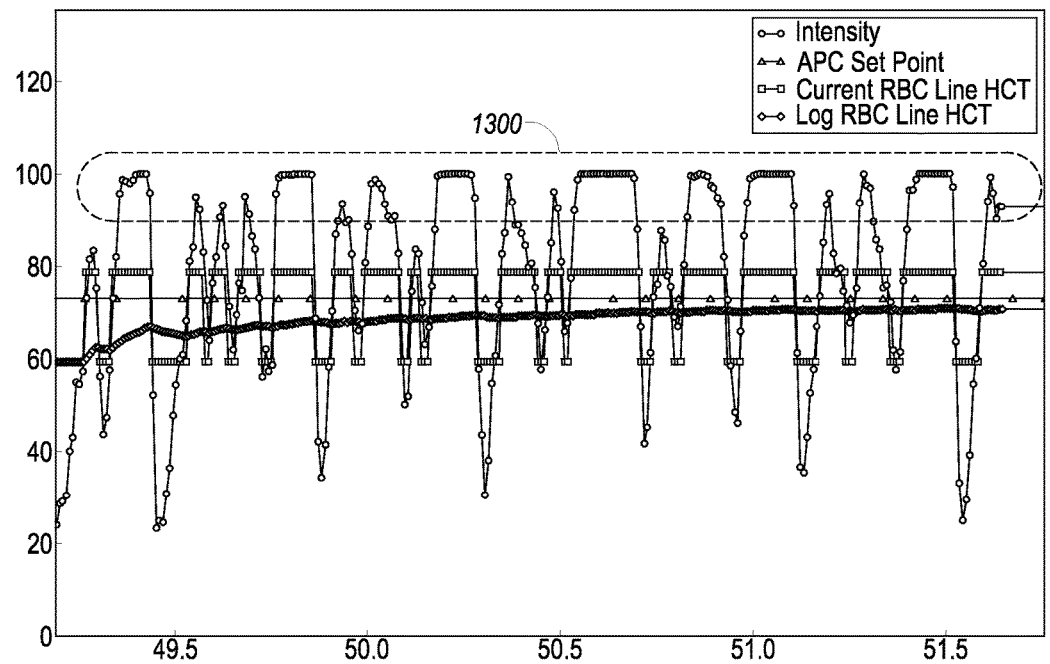
FIGS. 13-15 illustrate data regarding component(s) of whole blood that have been separated, and that may be received by an imaging system consistent with an embodiment.
Figure 14:
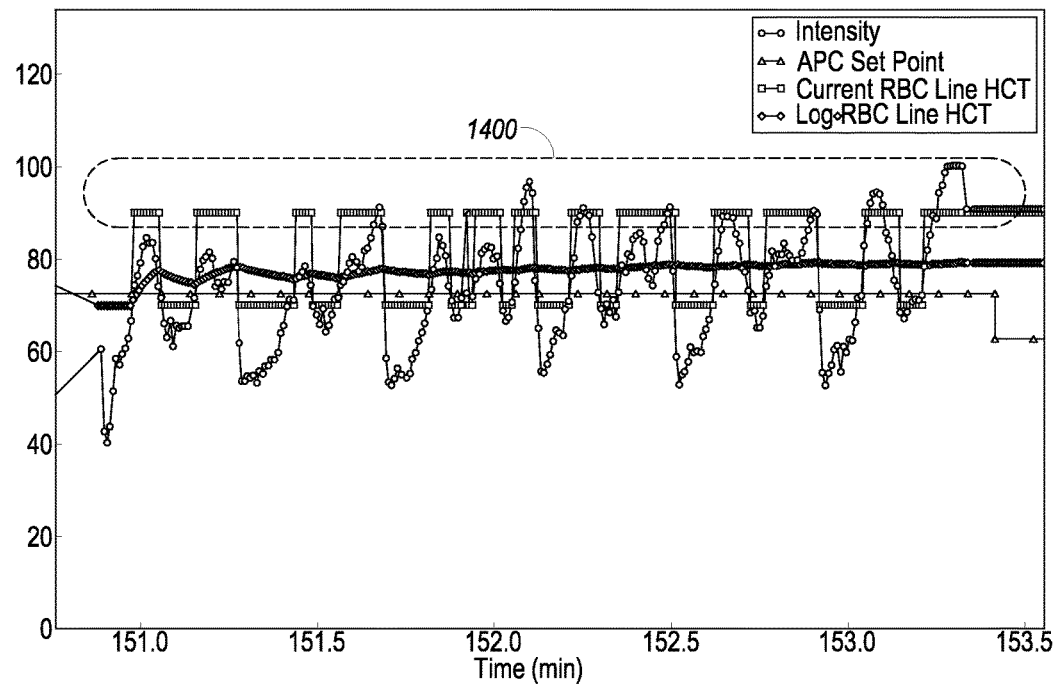
Figure 15:
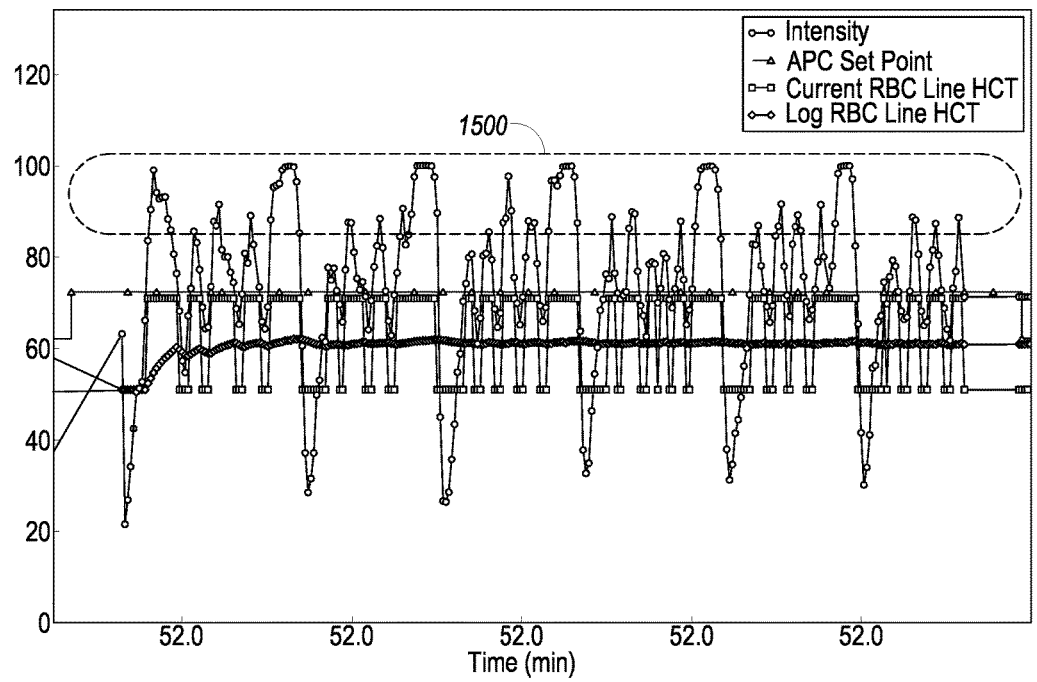

In embodiments, the data received at step 1208, as discussed above, may be data from an imaging system. Accordingly, a sub-step 1224 may be performed to calculate a metric from the data that has been received. FIGS. 13-15 illustrate examples of image data that may be received from a camera of an imaging system, in one embodiment. The data may be received during separation of whole blood into blood components.

FIG. 13 illustrates a graph showing, among other information, intensity of light (see peaks 1300) over some period of time, as received by an imaging system. For FIG. 13, the graphed data is generated from whole blood being separated that includes a relatively low concentration of platelets. As shown, the intensity remains at peak levels for significant periods of time, e.g., relatively long durations. FIG. 14 shows similar data as FIG. 13 but for whole blood with relatively high concentrations of platelets. In contrast to FIG. 13, the intensity remains relatively low and has peaks (see peaks 1400) for short periods of time, e.g., relatively short durations.

Finally, FIG. 15 shows data for whole blood with normal concentrations of platelets. As FIG. 15 shows, the intensity reaches peak levels (see peaks 1500) greater than those of FIG. 14 and similar to levels in FIG. 13, but for shorter periods of time. In embodiments, the data for different samples of whole blood with similar concentrations of platelets result in similar data.

In embodiments, as part of step 1220, data such as the data illustrated in FIGS. 13-15 is received and a metric is calculated at sub-step 1224. The metric is a value that may result from inputting the data (see FIGS. 13-15) into a function. The metric is therefore indicative of the relative amount of a component in the multi-component liquid, e.g., platelets in the whole blood.

Figure 16:
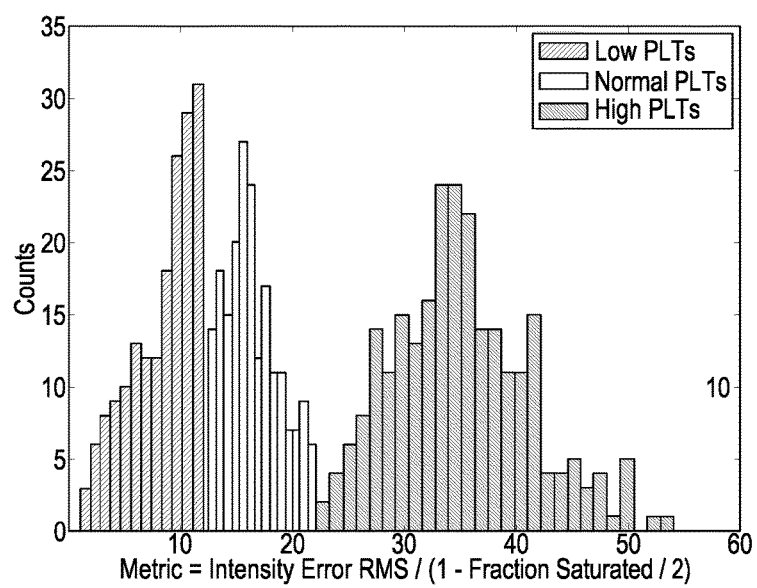
FIG. 16 illustrates a histogram showing one function that may be used to generate metrics according to an embodiment.

In some embodiments, the function used to generate the metric may generate metric values of between about 0 to about 60. FIG. 16 illustrates one example of a histogram showing a relationship between platelet concentrations and a metric that is generated using a specific function. The function used in this embodiment is: Metric=Intensity Error RMS/(1−(Fraction Saturated/2)). The Intensity Error root mean square (RMS), refers to the RMS of the difference between the actual light intensity that a camera may detect at a light detection port and a set point that may be set by an operator based on a collection preference, e.g., a light intensity associated with a collection location such as, at or above, an interface after separation of a liquid into components (see FIG. 9). The Fraction Saturated refers to the fraction of data points where the light intensity is saturated, in other words approximately 100% light is detected at the light detection port.

In the embodiment illustrated in FIG. 16, a metric value range of between about 0 and about 15 may indicate high platelet concentrations, a metric value range of between about 15 and about 22 may indicate normal platelet concentrations, and a metric value range of between about 22 and about 52 may indicate low platelet concentrations.

The specific embodiment illustrated in FIG. 16 is provided merely for illustrative purposes. In other embodiments, different functions may be used that generate different metric values. Any suitable function that generates metrics that allow for relative comparisons of component concentrations may be used and are within the scope of embodiments of the present invention.

Referring back to flow 1200, another sub-step 1228 that may be performed as part of step 1220 is to associate the data or calculated metric to a control gain. In some embodiments, when the data received at step 1208 is a concentration, sub-step 1228 may involve looking up the received concentration in a table that associates the concentration to control gain values. In other embodiments, a metric may be calculated at sub-step 1224 and the metric value may be used to find an associated control gain, e.g, by looking up the metric in a table that associates metrics to control gain values, in sub-step 1228. As one example, data/metric values that indicate a relatively low concentration of a component may be associated with lower control gain values while relatively higher concentrations may be associated with higher control gain values. However, in other embodiments, data/metric values that indicate a relatively low concentration of a component may be associated with higher control gain values while relatively higher concentrations may be associated with lower control gain values.

From step 1220, flow 1200 proceeds to step 1232 where data regarding position of an interface is received. The interface may be between two components that have been separated from a multi-component liquid. Step 1232 may be performed to determine where the interface is positioned relative to an inlet for a conduit. The conduit may be used to direct flow of one of the components, after separation from the multi-component liquid, into a collection container.

In embodiments, step 1232 may involve one or more sub-steps. For example, in one embodiment, an imaging system may transmit the data received at step 1232. In these embodiments, step 1232 may involve a sub-step 1236 of receiving data from an imaging system, such as imaging system 1100 (FIG. 11).

After step 1232, flow 1200 passes to step 1240 where the gain previously determined at step 1220 is used to change a position of the interface. In one embodiment, changing a position of the interface may involve changing a pump rate. Accordingly, at sub-step 1244 a pump rate may be changed, using the control gain determined at step 1220.

Flow then passes to step 1248 where the components separated from the composite liquid are collected. The components may be collected in various containers. For example, in an embodiment where whole blood is being separated, the blood components may be collected in bags that can then be used to later transfuse into a patient or further processed. From step 1248, some embodiments provide for looping back to step 1232 if the separation process is continuing. If a determination 1252 is made that the process is done, flow 1200 ends at 1256.

Although flow 1200 has been described with steps listed in a particular order, the present invention is not limited thereto. In other embodiments, steps may be performed in different order, in parallel, or any different number of times, e.g., before and after another step. Also, as indicated above, flow 1200 includes some optional steps/sub-steps. However, those steps above that are not indicated as optional should not be considered as essential to the invention, but may be performed in some embodiments of the present invention and not in others.

Figure 17:
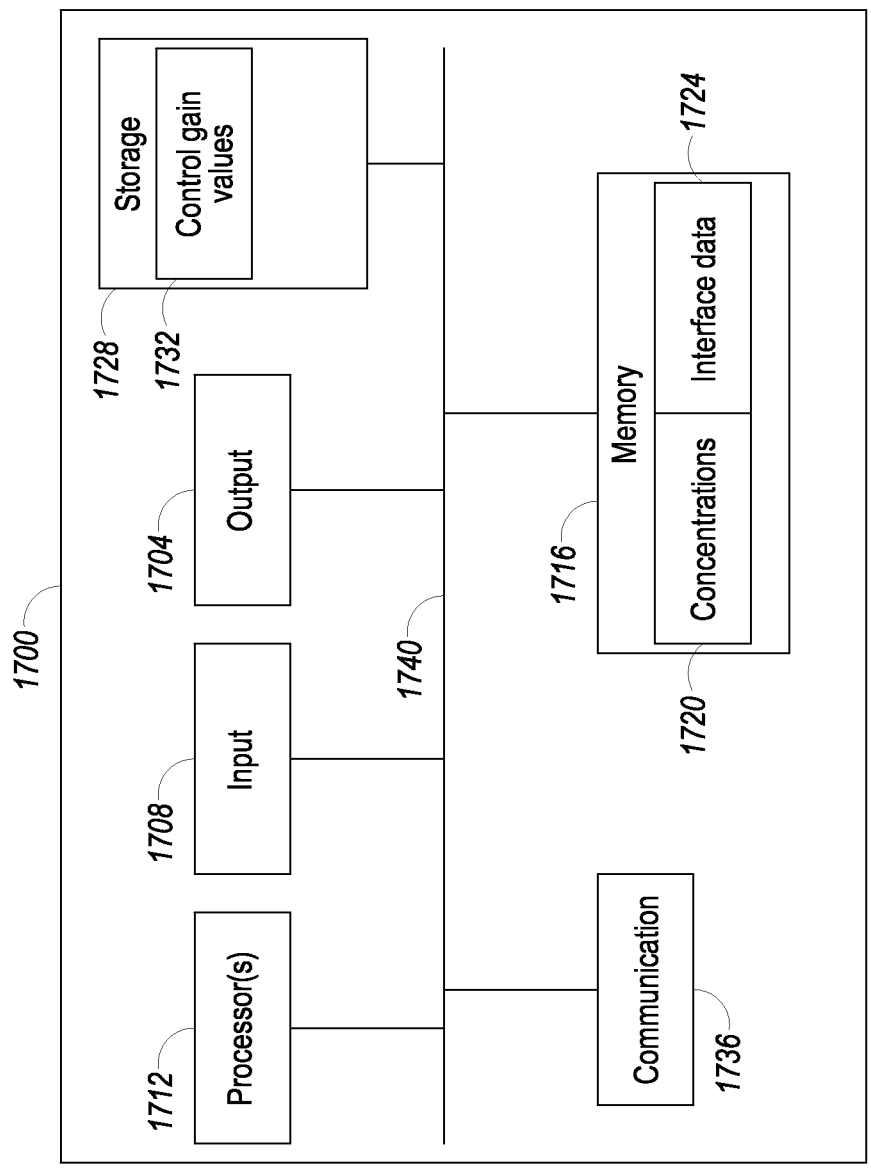
FIG. 17 illustrates a computer system on which some embodiments may be implemented.

FIG. 17 illustrates example components of a basic computer system 1700 upon which embodiments of the present invention may be implemented. For example, systems 100 (FIG. 1), 600 (FIG. 6), and 1100 (FIG. 11) may incorporate features of the basic computer system 1700 shown in FIG. 17. Computer system 1700 includes output device(s) 1704, and input device(s) 1708. Output device(s) 1704 may include, among other things, one or more displays, including CRT, LCD, and/or plasma displays. Output device(s) 1704 may also include printers, speakers etc. Input device(s) 1708 may include, without limitation, a keyboard, touch input devices, a mouse, voice input device, scanners, etc.

Basic computer system 1700 may also include one or more processor(s) 1712 and memory 1716, according to embodiments of the present invention. In embodiments, the processor(s) 1712 may be a general purpose processor(s) operable to execute processor executable instructions stored in memory 1716. Processor(s) 1712 may include a single processor or multiple processors, according to embodiments. Further, in embodiments, each processor may be a single core or a multi-core processor, having one or more cores to read and execute separate instructions. The processors may include, in embodiments, general purpose processors, application specific integrated circuits (ASICs), field programmable gate arrays (FPGAs), and other integrated circuits.

The memory 1716 may include any tangible storage medium for short-term or long-term storage of data and/or processor executable instructions. The memory 1716 may include, for example, Random Access Memory (RAM), Read-Only Memory (ROM), or Electrically Erasable Programmable Read-Only Memory (EEPROM). Other storage media may include, for example, CD-ROM, tape, digital versatile disks (DVD) or other optical storage, tape, magnetic disk storage, magnetic tape, other magnetic storage devices, etc.

Storage 1728 may be any long-term data storage device or component. Storage 1728 may include one or more of the devices described above with respect to memory 1716. Storage 1728 may be permanent or removable.

Computer system 1700 also includes communication devices 1736. Devices 1736 allow system 1700 to communicate over networks, e.g., wide area networks, local area networks, storage area networks, etc., and may include a number of devices such as modems, hubs, network interface cards, wireless network interface cards, routers, switches, bridges, gateways, wireless access points, etc.

The components of computer system 1700 are shown in FIG. 17 as connected by system bus 1740. It is noted, however, that in other embodiments, the components of system 1700 may be connected using more than a single bus.

In embodiments, system 100 (FIG. 1), module 120 (FIG. 1), processor 140 (FIG. 1), system 600 (FIG. 6), controller 716 (FIG. 7), and system 1100 (FIG. 11) may include aspects of system 1700. In these embodiments, memory 1716 may store concentrations of components 1720 or data regarding location of an interface 1724. In other embodiments, storage 1728 may store information associating data or metrics to control gains 1732.

It will be apparent to those skilled in the art that various modifications and variations can be made to the methods and structure of the present invention without departing from its scope. Thus it should be understood that the invention is not be limited to the specific examples given. Rather, the invention is intended to cover modifications and variations within the scope of the following claims and their equivalents.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the claimed invention.

What is claimed is:

1. A method of separating components from whole blood, the method comprising:
    receiving, by at least one processor, a first data related to a first platelet concentration in a first whole blood;
    separating, with a separator, the first whole blood into at least a first buffy coat and first red blood cells;
    determining, by the at least one processor, a first gain based on the first data related to the first platelet concentration;
    using the first gain in controlling a position of an interface between the first buffy coat and the first red blood cells by using the first gain when changing a speed of a pump that pumps one or more of the first buffy coat and the first red blood cells;
    receiving, by the at least one processor, a second data related to a second platelet concentration in a second whole blood, wherein the second platelet concentration is different from the first platelet concentration;
    separating, with the separator, the second whole blood into a second buffy coat and second red blood cells;
    determining, by the at least one processor, a second gain based on the second data related to the second platelet concentration, wherein the second gain is different from the first gain; and
    using the second gain in controlling a position of an interface between the second buffy coat and the second red blood cells by using the second gain when changing a speed of the pump that pumps one or more of the second buffy coat and the second red blood cells.

2. The method of claim 1, wherein the first data related to the first platelet concentration is light intensity data corresponding to the first platelet concentration in the first whole blood.

3. The method of claim 2, wherein the first data related to the first platelet concentration is captured by an imaging system.

4. The method of claim 1, wherein the determining, by the at least one processor, a first gain, comprises:
    calculating, by the at least one processor, a metric based on the first data related to the first platelet concentration.

5. The method of claim 4, wherein the determining, by the at least one processor, the first gain, further comprises:
    selecting the first gain based on the metric.

6. The method of claim 1, further comprising:
    after the determining, by the at least one processor, the first gain, receiving data regarding the position of the interface between the first buffy coat and the first red blood cells.

7. The method of claim 6, wherein the data regarding the position of the interface between the first buffy coat and the first red blood cells is light intensity data.

8. The method of claim 7, wherein the data regarding the position of the interface between the first buffy coat and the first red blood cells is captured by an imaging system.

9. The method of claim 6, further comprising:
based on the data regarding the position of the interface between the first buffy coat and the first red blood cells, moving the position of the interface between the first buffy coat and the first red blood cells.

10. The method of claim 9, wherein the moving the position of the interface between the first buffy coat and the first red blood cells comprises changing a speed of the pump pumping one of the one or more of the first buffy coat and the first red blood cells.

11. The method of claim 2, wherein the second data related to the second platelet concentration is second light intensity data corresponding to the second platelet concentration in the first whole blood.

12. The method of claim 11, wherein the second data related to the second platelet concentration is captured by the imaging system.

13. The method of claim 5, wherein the determining, by the at least one processor, the second gain, comprises:
calculating, by the at least one processor, a second metric based on the second data related to the second platelet concentration, wherein the second metric is different from the first metric.

14. The method of claim 13, wherein the determining, by the at least one processor, the second gain, further comprises:
selecting the second gain based on the second metric.

15. The method of claim 6, further comprising:
after the determining the second gain, receiving data regarding the position of the interface between the second buffy coat and the second red blood cells.

16. The method of claim 15, wherein the data regarding the position of the interface between second buffy coat and the second red blood cells is second light intensity data.

17. The method of claim 16, wherein the data regarding the position of the interface between the second buffy coat and the second red blood cells is captured by the imaging system.

18. The method of claim 15, further comprising:
based on the data regarding the position of the interface between the second buffy coat and the second red blood cells, moving the position of the interface between the second buffy coat and the second red blood cells.

19. The method of claim 18, wherein the moving the position of the interface between the second buffy coat and the second red blood cells comprises changing a speed of the pump pumping one of the one or more of the second buffy coat and the second red blood cells.

* * * * *